United States Patent [19]
Martin et al.

[11] Patent Number: 5,999,886
[45] Date of Patent: Dec. 7, 1999

[54] MEASUREMENT SYSTEM FOR DETECTING CHEMICAL SPECIES WITHIN A SEMICONDUCTOR PROCESSING DEVICE CHAMBER

[75] Inventors: Michel A. Martin, Lafayette, Ind.; Richard J. Markle; James K. Fidler, both of Austin, Tex.

[73] Assignee: Advanced Micro Devices, Inc., Sunnyvale, Calif.

[21] Appl. No.: 08/923,492

[22] Filed: Sep. 5, 1997

[51] Int. Cl.$^6$ .................................................. G01N 27/00
[52] U.S. Cl. .............................. 702/31; 702/30; 702/138; 702/140; 702/184; 364/468.26; 364/468.28; 364/528.36
[58] Field of Search ................................. 702/31, 22–24, 702/25–30, 32, 81–84, 138, 140, 182–185, 189, 193; 230/492.2; 430/322–324, 297–299, 311–314; 73/23.2, 23.27, 23.21–23.23, 23.34–23.37, 23.41, 24.04, 29.01, 31.06; 422/83, 105, 108, 89, 98; 438/680, 3, 10–14, 17, 18, 905–907, 909, FOR 141; 364/468.16, 17, 468.26–28, 469.02, 528.01, 36

[56] References Cited

U.S. PATENT DOCUMENTS

| | | | |
|---|---|---|---|
| 5,014,217 | 5/1991 | Savage | 702/28 |
| 5,347,460 | 9/1994 | Gifford et al. | 364/468.28 |
| 5,444,637 | 8/1995 | Smesny et al. | 438/18 |
| 5,522,918 | 6/1996 | Shiramizu | 73/23.37 |
| 5,546,322 | 8/1996 | Gifford et al. | 702/32 |

*Primary Examiner*—Hal Wachsman
*Attorney, Agent, or Firm*—Kevin L. Daffer; Conley, Rose & Tayon

[57] ABSTRACT

A measurement system is presented for detecting the presence of one or more harmful chemical species within one or more chambers of a semiconductor wafer processing device. Chemical species of interest include oxygen ($O_2$), nitrogen ($N_2$), moisture ($H_2O$), and organic compounds associated with photoresist processing. Such organic compounds include isopropyl alcohol ($CH_3CH(OH)CH_3$), acetone ($CH_3COCH_3$), and ethyl-3-ethoxy propionate ($C_7H_{14}O_3$). Candidate semiconductor wafer processing devices include evaporation, sputtering, and low pressure chemical vapor deposition (LPCVD) devices. The measurement system measures the concentrations of chemical species within each monitored chamber of the semiconductor wafer processing device: (i) during the processing of semiconductor wafers within the semiconductor wafer processing device, and (ii) during recovery periods following preventive maintenance or repair activities performed upon the semiconductor wafer processing device. Performing measurements during recovery periods aids in returning the semiconductor wafer processing device to service following preventive maintenance or repair activities. Data collection is not performed at other times (e.g., when the semiconductor wafer processing device is idle) in order to reduce data storage requirements. The measurement system includes one or more ambient sampling sensors coupled to a data collection computer through a control interface. Each ambient sampling sensor is in gaseous communication with ambients within the one or more monitored chambers. The control interface triggers data collection during the processing of one or more semiconductor wafers within the semiconductor wafer processing device, and following a maintenance activity performed upon the semiconductor wafer processing device.

26 Claims, 4 Drawing Sheets

MEASUREMENT SYSTEM FOR DETECTING CHEMICAL SPECIES WITHIN A SEMICONDUCTOR PROCESSING DEVICE CHAMBER

BACKGROUND OF THE INVENTION

1. Field of the Invention

This invention relates to semiconductor wafer fabrication, and more particularly to the detection of harmful chemical species within a chamber of a semiconductor wafer processing device.

2. Description of the Relevant Art

In order to eliminate undesirable effects caused by the presence of chemical species normally found in the surrounding air, several semiconductor wafer fabrication operations are performed in a vacuum. Vacuum is a condition of low pressure, generally below standard atmospheric pressure. A vacuum is generally formed by evacuating air molecules from a chamber using a vacuum pump. Wafer fabrication processes performed in a vacuum include evaporation, sputtering, low pressure chemical vapor deposition (LPCVD), and ion implantation.

The first four wafer fabrication processes listed above are deposition processes used to deposit a layer of a select material upon an exposed surface of a semiconductor wafer. The air around us, exclusive of water vapor, is about 78 percent (by volume) nitrogen ($N_2$), 21 percent oxygen ($O_2$), and 1 percent other gases. The presence of oxygen and/or nitrogen within a deposition chamber during a deposition process may deleteriously affect the properties of the deposited layer. The air also contains moisture ($H_2O$) which may also negatively affect the properties of the deposited layer.

For example, one common material deposited upon semiconductor wafers is aluminum. Aluminum layers are chiefly patterned to form electrical conductors called interconnects. All four deposition processes involve liberating aluminum atoms from an aluminum source and depositing the aluminum atoms upon an exposed surface of a semiconductor wafer. If a large number of oxygen molecules are present within the deposition chamber during the deposition process, a substantial number of the aluminum atoms may combine with the oxygen atoms before reaching the exposed surface of the semiconductor wafer. Compounds thus formed containing aluminum and oxygen, including aluminum oxide (AlO) and aluminum trioxide ($Al_2O_3$), would be incorporated into the aluminum layer. Aluminum oxide and aluminum trioxide are dielectric materials, and their presence within the aluminum layer reduces the electrical conductivity of the aluminum layer. Successful deposition of aluminum, and any other select material which readily reacts with molecules found in the air to form undesirable compounds, must therefore be carried out in a vacuum. LPCVD is carried out at pressures down to about $1.0 \times 10^{-3}$ torr, while evaporation and sputtering involve pressures down to approximately $1.0 \times 10^{-9}$ torr.

A typical deposition system includes a load lock chamber and at least one deposition chamber. The load lock chamber includes a gas-tight door for loading containers of wafers to be processed into the load lock chamber and for unloading containers of processed wafers from the load lock chamber. A gas-tight portal separates the load lock chamber from the deposition chamber. During use, the deposition chamber is continuously maintained at an operating pressure below atmospheric pressure (i.e., under vacuum) while the load lock chamber is cycled between atmospheric pressure and the lower operating pressure for wafer container loading and unloading.

From time to time, deposition systems must be removed from service for preventive maintenance (e.g., scheduled component replacements) or repair operations. Under such conditions, the deposition chamber must often be returned to atmospheric pressure (i.e., "vented"). The venting of the deposition chamber allows air, including oxygen, nitrogen, and moisture, to enter the deposition chamber.

Following completion of the preventive maintenance or repair operations, the deposition chamber must be evacuated and sufficiently purged of the oxygen, nitrogen, and moisture before being returned to service. A period of time is allowed for "recovery" of the deposition system. Lacking any direct way to measure the concentrations of various chemical species within the deposition chamber during recovery, the amount of time allowed for recovery is typically based upon operator experience and/or test wafer results. An operator typically allows a recovery time which, in his or her experience, has not resulted in problems caused by the presence of oxygen, nitrogen, or moisture within the deposition chamber.

Chemical species present on surfaces of the wafers prior to deposition may also deleteriously affect the properties of deposited layers. For example, significant amounts of residual substances associated with photoresist processing, chiefly organic compounds, remaining on surfaces of semiconductor wafers following photolithographic patterning processes are known to negatively affect the properties of layers subsequently deposited upon the surfaces of the wafers.

It would thus be advantageous to have a system for directly measuring concentrations of chemical species within a deposition chamber of a deposition system. Such a measurement system would allow detection of harmful chemical species (e.g, oxygen, nitrogen, moisture, and/or organic compounds) within the deposition chamber in time to take corrective action before substantial product is lost. Such a measurement system would also reduce the ambiguity surrounding deposition system recovery operations, allowing deposition systems to be returned to service as quickly as possible following preventive maintenance or repair operations. The measurement system would also desirably measure residual substances emitted into the surrounding chamber to allow corrective techniques to either reduce those contaminants on the surface prior to processing, or to more accurately remove contaminants from the ambient in-situ.

SUMMARY OF THE INVENTION

The problems outlined above are in large part solved by a measurement system for detecting the presence of one or more chemical species within one or more chambers of a semiconductor wafer processing device. The measurement system measures the concentrations of harmful chemical species (e.g., oxygen, nitrogen, moisture, and organic compounds associated with semiconductor and/or integrated circuit fabrication) within each monitored chamber of the semiconductor wafer processing device: (i) during the processing of semiconductor wafers within the semiconductor wafer processing device, and (ii) during recovery periods following preventive maintenance or repair activities performed upon the semiconductor wafer processing device. During the processing of semiconductor wafers within the processing device, the presence of one or more of the harmful chemical species is detected in time to take corrective action before substantial product is lost. Measuring the concentrations of harmful chemical species within each monitored chamber during recovery periods allows the processing device to be returned to service as quickly as possible following preventive maintenance or repair activities. Data collection is advantageously not performed at other times (e.g., when the semiconductor wafer processing device is idle) in order to reduce data storage requirements.

The measurement system includes one or more ambient sampling sensors in gaseous communication with ambients within the chamber or chambers of the processing device. Each ambient sampling sensor receives a control signal and produces a data signal in response to the control signal. The data signal indicates the presence of the one or more chemical species within the monitored chamber. The measurement system also includes a control interface coupled to each ambient sampling sensor. The control interface asserts the control signal (i.e., triggers data collection) during the processing of one or more semiconductor wafers within the semiconductor wafer processing device, and following a maintenance activity performed upon the processing device. The control interface receives the resulting data signal from the ambient sampling sensor. The measurement system also includes a data collection computer coupled to the control interface. The data collection computer receives data signals from the control interface and stores the data signals.

Candidate semiconductor wafer processing devices include evaporation, sputtering, and low pressure chemical vapor deposition (LPCVD) devices. As used herein, the term "deposition system" encompasses evaporation, sputtering, and low pressure chemical vapor deposition (LPCVD) devices. It is noted that the measurement system may also be used to monitor the concentrations of the one or more chemical species within one or more chambers of other types of semiconductor wafer processing devices.

Chemical species of interest include oxygen ($O_2$), nitrogen ($N_2$), moisture ($H_2O$), and organic compounds associated with photoresist processing. Such organic compounds include isopropyl alcohol ($CH_3CH(OH)CH_3$), acetone ($CH_3COCH_3$), and ethyl-3-ethoxy propionate ($C_7H_{14}O_3$).

Each ambient sampling sensor may be, for example, an individual oxygen, nitrogen, moisture, or organic compound sensor, or any combination thereof. In a preferred embodiment, each ambient sampling sensor is a quadrupole mass spectrometer detector which performs spectral scanning to determine the concentrations of chemical species in a gas mixture by atomic mass unit (AMU). In one embodiment, the ambient sampling sensor produces an analog data signal in response to the control signal. The control interface converts the analog data signal to a digital data signal and provides the digital data signal to the data collection computer.

The control interface receives one or more processing signals. Each processing signal is produced by a processing sensor, and indicates the processing of semiconductor wafers within a chamber of the semiconductor wafer processing device. In one embodiment, such processing signals are active high digital signals which are asserted when one or more semiconductor wafers are being processed in a corresponding chamber. The control interface also receives a pressure signal. In one embodiment, the pressure signal is produced by a manometer monitoring the pressure within a chamber of the semiconductor wafer processing device which is evacuated during normal operation. The pressure signal is an analog signal which varies from about 0.0 volts to approximately 10.0 volts over a respective pressure range of about 0.0 torr to approximately 1.0 torr. Normal to operation of the semiconductor wafer processing device corresponds to a monitored pressure of about $1.0 \times 10^{-7}$ torr. The present value of the pressure signal indicates normal operation of the semiconductor wafer processing device. The past values of the pressure signal indicate the performance of a maintenance activity upon the semiconductor wafer processing device, which typically involves the venting of the chamber monitored by the manometer to atmospheric pressure. The control interface asserts the control signal dependent upon the one or more processing signals and upon the present and past values of the pressure signal.

In one embodiment, the control interface comprises one or more logic controllers and a logic circuit. Each logic controller is coupled between a corresponding ambient sampling sensor and the data collection computer. Each logic controller receives the manometer pressure signal and a maintenance signal which indicates the performance of maintenance upon the deposition system. In one embodiment there are multiple processing signals, and each logic controller also receives a logical OR of the one or more processing signals. Each logic controller produces the control signal which triggers data collection dependent upon the manometer pressure signal, the maintenance signal, and the logical OR of the one or more processing signals. Each logic controller also produces a second and third pressure signals dependent upon the manometer pressure signal.

The logic circuit receives the one or more processing signals and the second and third pressure signals. The logic circuit produces the logical OR of the one or more processing signals and provides the logical OR of the one or more processing signals to each logic controller. The logic circuit produces the maintenance signal dependent upon the second and third pressure signals and the logical OR of the one or more processing signals, and provides the maintenance signal to each logic controller.

The logic circuit includes a select switch and a maintenance switch. The select switch has an automatic position and a manual position. When the select switch is in the automatic position, the logic circuit produces the maintenance signal dependent upon the second and third pressure signals. When the select switch is in the manual position, the logic circuit produces the maintenance signal when a user activates the maintenance switch.

Each logic controller asserts the second and third pressure signals when the manometer pressure signal indicates a pressure greater than a first and second threshold values, respectively. The first and second threshold values are selected such that the second threshold value is greater than the first threshold value, and both the first and second threshold values exceed the normal operating pressure (i.e., $1.0 \times 10^{-7}$ torr). In one embodiment, the first threshold value is about 0.05 torr and the second threshold value is approximately 0.1 torr. The logic circuit asserts the maintenance signal when both the first and second pressure signals are asserted and the manometer pressure signal is asserted before the second pressure signal, indicating an increase in the manometer pressure signal above a value associated with the normal operating pressure. The increase is typically due to the return of the chamber monitored by the manometer to atmospheric pressure (i.e., the venting of the chamber monitored by the manometer) during a maintenance activity.

Once the logic circuit asserts the maintenance signal, the logic circuit continues to assert the maintenance signal until the manometer pressure signal indicates a return to normal operation and the one or more processing signals indicate the processing of one or more semiconductor wafers within the one or more chambers of the semiconductor wafer processing device.

Each ambient sampling sensor is preferably a quadrupole mass spectrometer detector capable of operating in either a scanning mode, an idle mode, or a shutdown mode. The operating mode is dependent upon one or more control signals produced by the corresponding logic controller of the control interface. A given ambient sampling sensor produces analog data signals when operating in the scanning mode. In the idle mode, an ambient sampling sensor is made ready to perform the spectrum scanning function, but is not actively producing analog data signals. All power is removed from a sensor head of the ambient sampling sensor in the shutdown mode in order to protect the filaments of the ambient sampling sensor from an oxygen-rich environment.

Each logic controller issues the one or more control signals placing the corresponding ambient sampling sensor in the scanning mode when the pressure within the chamber monitored by the manometer is less than a third threshold value and at least one of the one or more processing signals is asserted. In one embodiment, the third threshold value is about 0.01 torr. Each logic controller also issues the one or more control signals placing the corresponding ambient sampling sensor in the scanning mode when the pressure within the chamber monitored by the manometer exceeds the third threshold value and the maintenance signal is asserted. Each logic controller issues the one or more control signals placing the corresponding ambient sampling sensor in the idle mode when the pressure within the chamber monitored by the manometer is less than the third threshold value, all of the one or more processing signals are deasserted, and the maintenance signal is deasserted. Each logic controller issues the one or more control signals placing the corresponding ambient sampling sensor in the shutdown mode when the pressure within the chamber monitored by the manometer is greater than the third threshold value.

BRIEF DESCRIPTION OF THE DRAWINGS

Other objects and advantages of the invention will become apparent upon reading the following detailed description and upon reference to the accompanying drawings in which.

Figure 1:
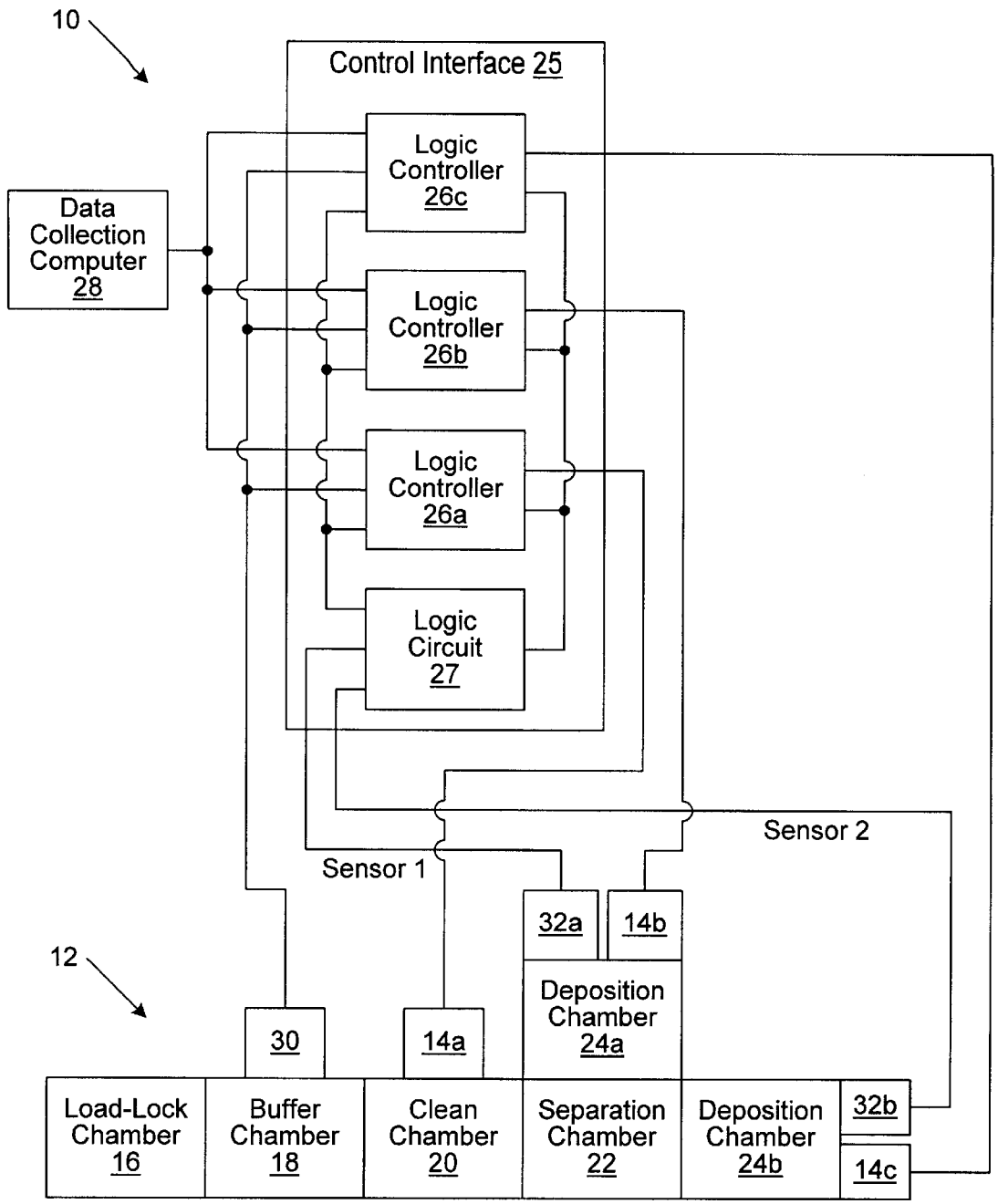
FIG. 1 is a block diagram of a measurement system of the present invention connected to a deposition system, wherein the measurement system includes multiple ambient sampling sensors coupled to a data collection computer through a control interface, and wherein the control interface includes multiple logic controllers and a logic circuit, and wherein the measurement system detects the presence of harmful chemical species (i.e., oxygen, nitrogen, moisture, and organic compounds associated with photoresist processing) within each monitored chamber of the deposition system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the figures, FIG. 1 is a block diagram of a measurement system 10 connected to a wafer fabrication system, e.g. a deposition system 12. Measurement system 10 includes three ambient sampling sensors 14a–c in gaseous communication with three different chambers of deposition system 12. Measurement system 10 measures the concentrations of harmful chemical species (e.g., oxygen, nitrogen, moisture, and organic compounds associated with photoresist processing) within each monitored chamber of deposition system 12 during the processing of semiconductor wafers within deposition it) system 12. Detection of the presence of one or more of the harmful chemical species occurs with sufficient time to take corrective action before substantial product is lost. Measurement system 10 also measures the concentrations of harmful chemical species within each monitored chamber of deposition system 12 during recovery periods following preventive maintenance or repair activities performed upon deposition system 12, allowing deposition system 12 to be returned to service as quickly as possible following the preventive maintenance or repair activities.

Deposition system 12 includes a load-lock chamber 16, a buffer chamber 18, a clean chamber 20, a separation chamber 22, and two deposition chambers 24a–b. The manufacture and operation of such deposition systems are well known. Load-lock chamber includes a gas-tight door (not shown) for loading containers of wafers to be processed into the load lock chamber and for unloading containers of processed wafers from the load lock chamber. A container originally containing wafers to be processed remains in load-lock chamber 16 during processing of the wafers through buffer chamber 18, clean chamber 20, separation chamber 22, and deposition chamber 24a or 24b.

Buffer chamber 18 adjoins load-lock chamber 16. A gas-tight portal (not shown) exists between load lock chamber 16 and buffer chamber 18. Wafers are removed from the container within load-lock chamber 16 and transferred as a group to buffer chamber 18. Buffer chamber 18 permits temporary storage of a group of wafers during container loading or unloading within load-lock chamber 16. During operation of deposition system 12, a substantially constant pressure of about $1.0 \times 10^{-7}$ torr is maintained within buffer chamber 18. From this point on, wafers are processed individually. Wafers are separated from the group and processed one after another in sequence through clean chamber 20, separation chamber 22, and deposition chamber 24a or 24b.

Clean chamber 20 adjoins buffer chamber 18. A gas-tight portal (not shown) exists between buffer chamber 18 and clean chamber 20. Within clean chamber 20, wafers are individually heated to about 250 deg. C for a period of time sufficient to drive volatile substances out of the wafers (i.e., to "degass" the wafers) in preparation for subsequent deposition. The pressure within clean chamber 18 is nominally maintained at about $1.0 \times 10^{-7}$ torr. During heating of the wafers, the pressure within clean chamber 18 rises due to outgassing of the wafers. A typical maximum pressure value during heating is about $5.0 \times 10^{-6}$ torr.

Separation chamber 22 adjoins clean chamber 20. A gas-tight portal (not shown) exists between clean chamber 20 and separation chamber 22. Separation chamber 22 also adjoins deposition chamber 24a and deposition chamber 24b. From separation chamber 22, a given wafer may be routed to deposition chamber 24a or 24b. Separation chamber 22 thus provides a common staging area for separate deposition chambers 24a–b.

A gas-tight portal (not shown) exists between separation chamber 22 and deposition chamber 24a, and between separation chamber 22 and deposition chamber 24b. Within deposition chamber 24a or 24b, a layer of a select material is deposited upon one or more exposed surfaces of a wafer. The pressures within deposition chambers 24a–b may be nominally maintained at about $1.0 \times 10^{-7}$ torr during certain operations of deposition system 12.

For example, deposition chamber 24a may be used for titanium (Ti) deposition, and deposition chamber 24b may be used to deposit titanium nitride (TiN). In this case, the pressures within deposition chambers 24a–b during deposition typically rise to steady values between $1.0 \times 10^{-3}$ and $1.0 \times 10^{-2}$ torr.

Following deposition, the wafers are transferred from deposition chamber 24a or 24b to separation chamber 22, from separation chamber 22 to clean chamber 20, then from clean chamber 20 to buffer chamber 18. Once all of the wafers have been processed, they are returned as a group to the original cassette present within load-lock chamber 16.

Deposition system 12 may be, for example, an Anelva Model 1015 Sputter System (Anelva, Tokyo, Japan). Deposition chambers 24a–b may be two of the three deposition chambers of the Anelva Model 1015 Sputter System. Alternately, deposition system 12 may be an evaporation, sputtering, or low pressure chemical vapor deposition (LPCVD) device.

Ambient sampling sensors 14a–c detect the presence of harmful chemical species, (e.g., oxygen, nitrogen, moisture, and organic compounds associated with photoresist processing) within corresponding monitored chamber of deposition system 12. Ambient sampling sensors 14a–c are preferably quadrupole mass spectrometer detectors which perform spectral scanning to determine the concentrations of chemical species in a gas mixture by atomic mass unit (AMU). One AMU is equal to about $1.66 \times 10^{-27}$ kilogram (kg). Molecules of oxygen ($O_2$), nitrogen ($N_2$), and moisture (i.e., water or $H_2O$) have masses of approximately 32, 28, and 18 AMUs, respectively. Organic compounds have various masses depending upon their chemical compositions. A suitable quadrupole mass spectrometer detector may be the MPA Micropole Analyzer (Ferran Scientific, Inc., San Diego, Calif.). The MPA Micropole Analyzer is capable of less than 1 AMU resolution within a 2 to 65 AMU range when operated at a maximum pressure of $5.0 \times 10^{-3}$ torr. The molecular masses of oxygen, nitrogen, and moisture are within the detection range of the MPA Micropole Analyzer. In addition, important organic compounds associated with photoresist processing, namely isopropyl alcohol $CH_3CH(OH)CH_3$, acetone $CH_3COCH_3$, and ethyl-3-ethoxy propionate $C_7H_{14}O_3$, have respective molecular masses of about 45, 58, and 59 AMUs which are also within the detection range of the MPA Micropole Analyzer. Alternately, each ambient sampling sensor 14 may be an individual oxygen, nitrogen, moisture, or organic compound detector, or any combination thereof.

In addition to ambient sampling sensors 14a–c, measurement system 10 includes a control interface 25 and a data collection computer 28. Control interface 25 is coupled between ambient sampling sensors 14a–c and data collection computer 28. Control interface 25 controls the operations of ambient sampling sensors 14a–c. For example, in cases where ambient sampling sensors 14a–c are MPA Micropole Analyzers, control interface 25 determines the operating modes of ambient sampling sensors 14a–c by issuing one or more control signals to ambient sampling sensors 14a–c. Each ambient sampling sensor 14 employs an electron beam, generated by a tungsten filament, to ionize gaseous molecules. An electric current is passed through the tungsten filament so as to heat the tungsten filament to incandescence. In this state, the tungsten filament gives off electrons through thermionic emission. In an oxygen-rich environment, the tungsten filament would rapidly oxidize (i.e., "burn up") and would be destroyed. The tungsten filament must therefore not be operated at pressures exceeding about 0.02 torr.

Where ambient sampling sensors 14a–c are MPA Micropole Analyzers, ambient sampling sensors 14 have a scanning mode, an idle mode, and a shutdown mode. In the scanning mode, a given ambient sampling sensor 14 performs spectral scanning to determine the concentrations of gaseous chemical species within the corresponding chamber of deposition system 12. In the idle mode, the ambient sampling sensor 14 is made ready to perform spectral scanning but does not perform spectral scanning. In the scanning and idle modes, the tungsten filament is active (i.e., electrical current is passed through the filament). In the shutdown mode, the tungsten filament is not active (i.e., electrical current is not passed the filament). Control interface 25 places ambient sampling sensors 14a–c in the shutdown mode to protect ambient sampling sensors 14a–c from an oxygen-rich environment.

Control interface 25 receives a pressure signal produced by a manometer 30 and two processing signals 'Sensor1' and 'Sensor2' produced by respective processing sensors 32a and 32b. Manometer 30 is in gaseous communication with buffer chamber 18 of deposition system 12, and measures the pressure within buffer chamber 18. Manometer may be part of measurement system 10, or may be part of deposition system 12. As described above, buffer chamber 18 is maintained at a substantially constant pressure of about $1.0 \times 10^{-7}$ torr during normal operation of deposition system 12. Manometer 30 produces a pressure signal which indicates the pressure within buffer chamber 18. The pressure signal is an analog signal which varies from about 0.0 volts to approximately 10.0 volts over a respective pressure range of about 0.0 torr to approximately 1.0 torr. Control interface 25 uses the pressure signal to determine the operating modes of ambient sampling sensors 14a–c. It is noted that the pressure within buffer chamber 18 is used to perform this function as buffer chamber 18 is the first chamber of deposition system 12 to be returned to atmospheric pressure during repair and periodic maintenance operations and the last chamber to be evacuated following repair and periodic maintenance operations.

Processing sensors 32a–b may be part of measurement system 10, or may be part of deposition system 12. Processing sensor 32a is associated with deposition chamber 24a, and asserts an active high 'Sensor1' logic signal when wafers are being processed within deposition chamber 24a. Processing sensor 32b is associated with deposition chamber 24b, and asserts an active high 'Sensor2' logic signal when wafers are being processed within deposition chamber 24b. An asserted 'Sensor1' or 'Sensor2' signal indicates that wafers are undergoing processing within the corresponding deposition chamber 24 of deposition system 12. The 'Sensor1' and 'Sensor2' signals are used to trigger automatic data collection during wafer processing.

In the scanning mode, a given ambient sampling sensor 14 performs spectral scanning to determine the concentrations of gaseous chemical species within the corresponding chamber of deposition system 12. The ambient sampling sensor 14 produces analog data signals representing the concentrations of one or more gaseous chemical species within the monitored chamber. Control interface 25 converts the analog data signals to corresponding digital data signals, and provides the digital data signals to data collection computer 28. Data collection computer 28 stores the digital data in a memory system (not shown). Data collection computer 28 performs various "data reduction" operations upon the digital data, producing the concentrations of gaseous chemical species within the corresponding chamber of deposition system 12 from the "raw" digital data. Data collection computer 28 may also issue one or more control signals to control interface 25 to initiate data collection.

Figure 2:
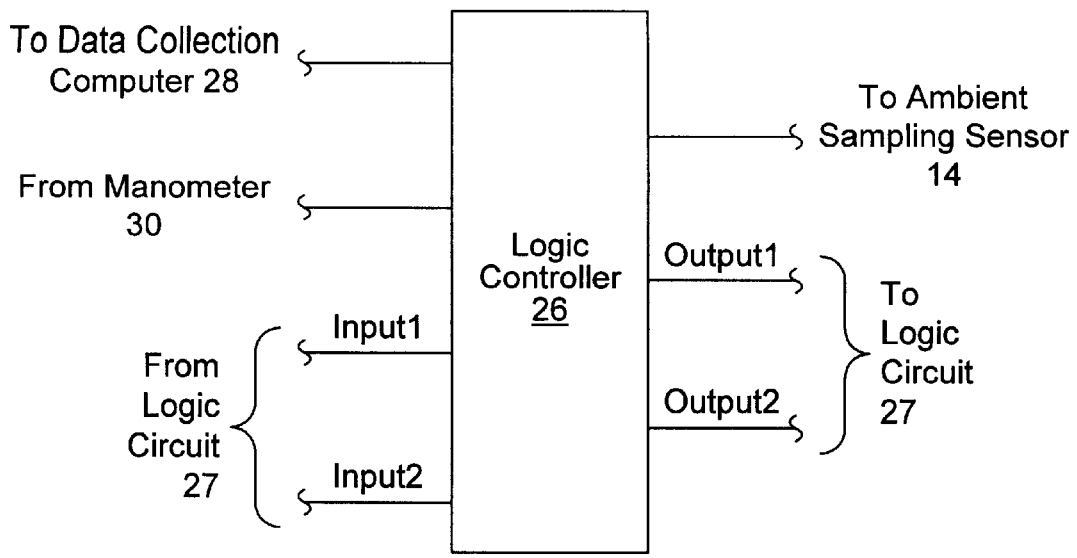
FIG. 2 is a block diagram of one embodiment of each logic controller of the control interface of FIG. 1, wherein each logic controller is coupled between the data collection computer and a corresponding ambient sampling sensor.

Control interface 25 includes three logic controllers 26a–c and a logic circuit 27. Logic controllers 26a–c are coupled between respective ambient sampling sensors 14a–c and data collection computer 28. Logic circuit 27 is coupled to each logic controller 26. Each logic controller 26 controls the operation of the corresponding ambient sampling sensor 14. FIG. 2 is a block diagram of one embodiment of each logic controller 26 of FIG. 1. During data collection, a given logic controller 26 issues one or more control signals to the corresponding ambient sampling sensor 14. The ambient sampling sensor 14 responds by producing an analog data signal which indicates the concentrations of one or more gaseous chemical species within the monitored chamber. The logic controller 26 receives the analog data signal and converts the analog data signals to a corresponding digital data signal. The logic controller then provides the digital data signal to data collection computer 28. Each logic controller 26 also produces output signals 'Output1' and 'Output2' based upon the pressure signal from manometer 30. In the present embodiment, signals 'Output1' and "Output2' are active low logic signals asserted when the pressure within buffer chamber 18 exceeds 0.05 torr and 0.1 torr, respectively.

Figure 3:
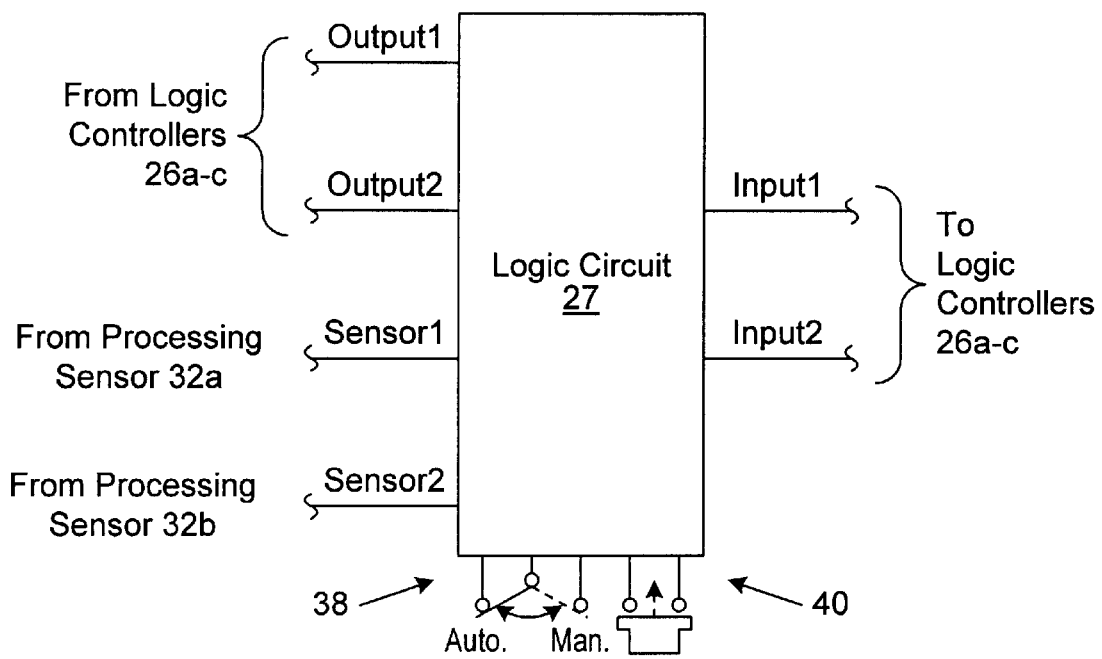
FIG. 3 is a block diagram of one embodiment of the logic circuit of FIG. 1, wherein the logic circuit receives output signals produced by each logic controller and produces input signals received by each logic controller.

FIG. 3 is a block diagram of one embodiment of logic circuit 27. Logic circuit 27 receives signals 'Output1' and 'Output2' form each logic controller 26. Logic circuit 27 also receives processing signals 'Sensor1' and 'Sensor2' produced by processing sensors 32a–b, respectively. Logic circuit 27 includes a select switch 38 and a preventive maintenance (PM) recovery switch 40. Logic circuit 27 produces output signals 'Input1" and 'Input2' based upon signals 'Output1' and 'Output2', the 'Sensor1' and 'Sensor2' signals produced by processing sensors 32a–b, and the status of select switch 38 and preventive maintenance (PM) recovery switch 40. In the present embodiment, output signals 'Input1' and 'Input2' are active high logic signals. The 'Input1' signal is asserted following, preventive maintenance or repair activities, allowing the monitoring of chemical species within the monitored chambers of deposition system 12 during subsequent recovery periods. The 'Input2' signal is asserted when wafers are being processed within deposition chamber 24a or 24b, allowing the measurement of chemical species concentrations within the monitored chambers during wafer processing.

Select switch 38 has two positions: 'automatic" and 'manual'. Placing, select switch 38 in the automatic position enables automatic data collection during the processing of wafers within deposition chamber 24a or 24b and following preventive maintenance and repair activities. When select switch 38 is in the automatic position, logic circuit 27 asserts the 'Input1' signal when the pressure within buffer chamber 18 increases substantially above the nominal pressure of $1.0 \times 10^{-7}$ torr present within buffer chamber 18 during normal operation. Such substantial pressure increases occur when buffer chamber 18 is vented to atmospheric pressure during repair or preventive maintenance activities. Placing select switch 38 in the manual position enables data collection following preventive maintenance and repair activities (i.e., during recovery periods). PM recovery switch 40 is a normally open momentary push-button switch. Pressing PM recovery switch 40 after placing select switch 38 in the manual position also causes logic circuit 27 to assert output signal 'Input1'.

Logic circuit 27 asserts the output signal 'Input2' when an asserted 'Sensor1' or 'Sensor2' signal is received from processing sensors 32a–b (i.e., wafers are being processed within deposition chamber 24a or 24b). Assertion of output signal 'Input2' is independent of the status of select switch 38 and PM recovery switch 40.

Each logic controller 26 produces one or more control signals coupled to the corresponding ambient sampling sensor 14 which determine the operating mode of the ambient sampling sensor 14. The one or more control signals are produced dependent upon the pressure signal from manometer 30 and input signals 'Input1' and 'Input2'. The one or more control signals cause the corresponding ambient sampling sensor 14 to transition to the scanning mode when the pressure within buffer chamber 18 is below 0.01 torr and the 'Input1' signal or the 'Input2' signal is asserted. Thus each logic controller 26 directs data collection when the pressure within buffer chamber 18 is below 0.01 torr and wafers are being processed within deposition chamber 24a or 24b (i.e., the 'Input2' signal is asserted). Each logic controller 26 also directs data collection when the pressure within buffer chamber 18 is below 0.01 torr and data collection during recovery following repair or maintenance activities is indicated (i.e., signal 'Input1' is asserted).

Each logic controller 26 issues one or more control signals which cause the corresponding ambient sampling sensor 14 to transition to the idle mode when the pressure within buffer chamber 18 is below 0.01 torr, wafers are not being processed within deposition chamber 24a or 24b, and data collection during the recovery period following a repair or maintenance activity has not been enabled. Each logic controller 26 issues one or more control signals which cause the ambient sampling sensor 14 to transition to the shutdown mode when the pressure signal from manometer 30 indicates the pressure within buffer chamber 18 is above 0.01 torr.

Figure 4:
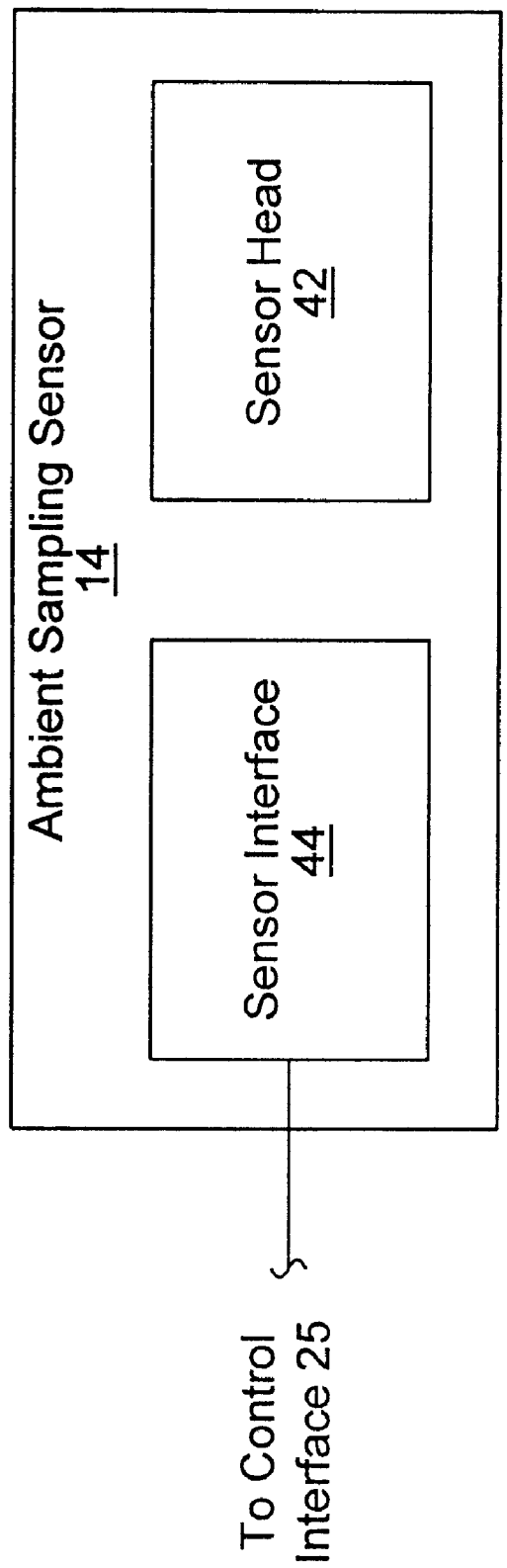
FIG. 4 is a block diagram of one embodiment of each ambient sampling sensor of FIG. 1, wherein each ambient sampling sensor includes a sensor head in gaseous communication with a corresponding chamber of the deposition system and a sensor interface coupled between sensor head and the control interface.

FIG. 4 is a block diagram of on embodiment of each ambient sampling sensor 14 of FIG. 1. Each ambient sampling sensor 14 includes a sensor head 42 and a sensor interface 44 coupled between sensor head 42 and the corresponding logic controller 26 of control interface 25. Sensor head 42 is in gaseous communication with the corresponding monitored chamber of deposition system 12. Sensor head 42 includes the sensing elements used to detect the presence of harmful chemical species, (e.g., oxygen, nitrogen, moisture, and organic compounds associated with photoresist processing) within the corresponding monitored chamber. Sensor head 42 produces data signals in response to one or more control signals received from the corresponding logic controller 26. Sensor interface 44 functions as an electrical interface between sensor head 42 and the corresponding logic controller 26. Sensor interface 44 may, for example, amplify, filter, and/or provide driver circuitry for the data signals produced by sensor head 42. A suitable sensor head 42 is the MPA Micropole Analyzer (Ferran Scientific, Inc., San Diego, Calif.). A suitable sensor interface 44 is the SC3 Spectra Converter Module (Ferran Scientific, Inc., San Diego, Calif.).

Figure 5:
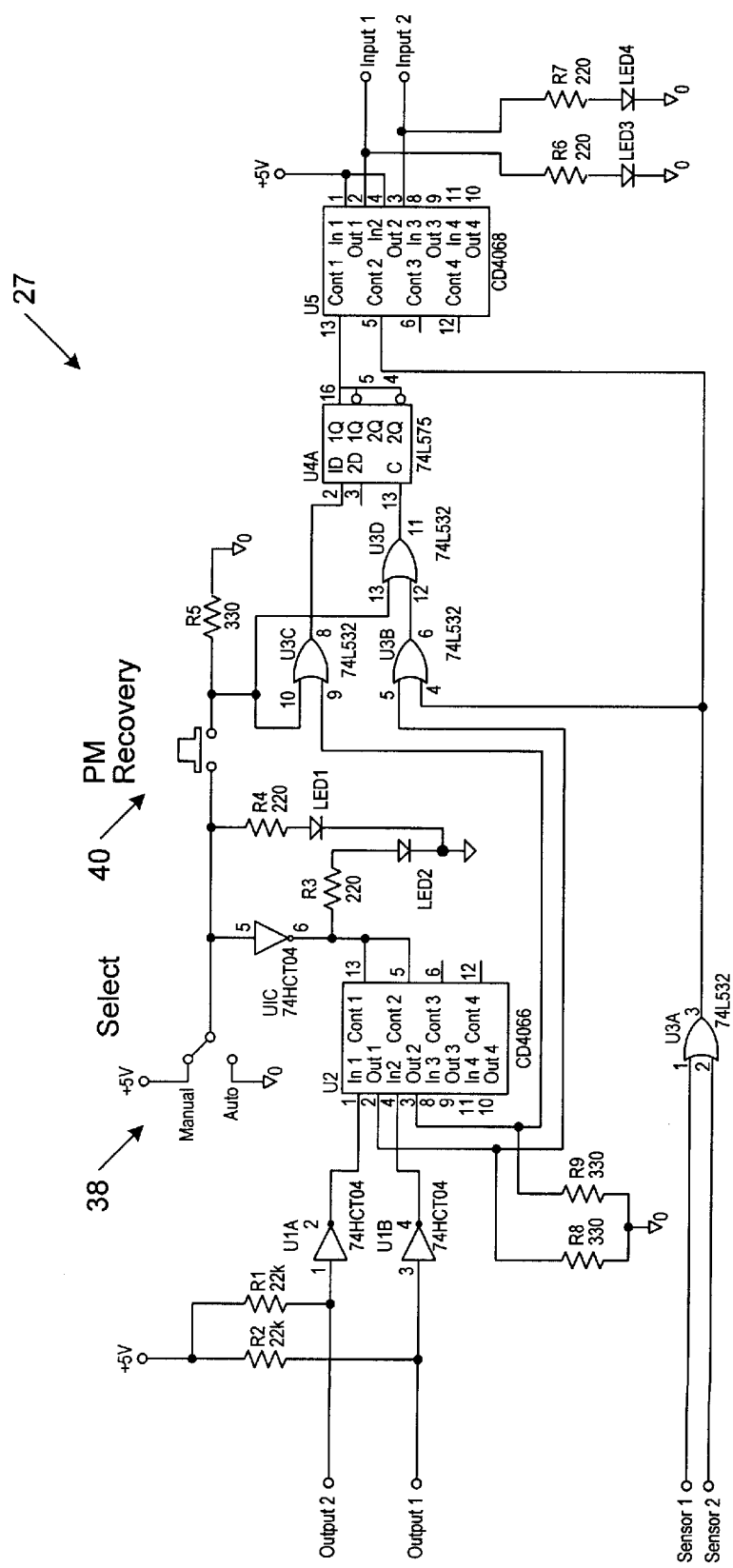
FIG. 5 is a circuit diagram of one embodiment of the logic circuit of FIG. 3.

FIG. 5 is a circuit diagram of one embodiment of logic circuit 27 of FIG. 2. Signals 'Output1' and 'Output2', produced by each logic controller 26, are produced at open-collector output terminals. Resistors R1 and R2 function as pullup resistors for the open-collector output terminals. Logic controller 26 produces signal 'Output1' having a value of about 5.0 volts when the pressure signal from manometer 30 indicates the pressure within buffer chamber 18 is below approximately 0.05 torr. Signal 'Output1' has a value of approximately 0.0 volts when the pressure signal from manometer 30 indicates the pressure within buffer chamber 18 is above 0.05 torr. Logic controller 26 also produces signal 'Output2' having a value of about 5.0 volts when the pressure signal from manometer 30 indicates the pressure within buffer chamber 18 is below approximately 0.1 torr. Signal 'Output2' has a value of approximately 0.0 volts when the pressure signal from manometer 30 indicates the pressure within buffer chamber 18 is above 0.1 torr. Two inverters invert the 'Output1' and 'Output2' logic signals for future processing.

A first complementary metal oxide semiconductor (CMOS) CD4066 switch allows for manual control of data collection following preventive maintenance and repair operations. Placing select switch 38 is in the manual position disconnects the 'Output1' and 'Output2' signals from the remaining logic circuitry. Pressing PM recovery switch 40 after placing select switch 38 in the manual position causes logic circuit 27 to assert output signal 'Input1'.

Signals 'Sensor1' and 'Sensor2' produced by processing sensors 32a and 32b, respectively, are logically ORed together within logic circuit 27. A second CD4066 CMOS switch produces signal 'Input2' having a value of about 5.0 volts when the 'Sensor1' signal or the 'Sensor2' signal is asserted, and approximately 0.0 volts otherwise. When select switch 38 is in the automatic position, the 'Sensor1' signal, 'Sensor2' signal, and the inverted 'Output1' signal are logically ORed to form an enable signal input ("C") to a 74LS75 transistor-transistor logic (TTL) D latch.

The D latch essentially produces the 'Input1' signal at a Q output terminal, with the second CD4066 CMOS switch buffering the 'Input1' signal. The D input is the inverted 'Output1' signal. The inverted 'Output1' signal is a logic low (i.e., a logic '0') when the pressure within buffer chamber 18 is less than 0.05 torr and a logic high (i.e., a logic '1') when the pressure within buffer chamber 18 is greater than 0.05 torr. Thus when select switch 38 is in the automatic position, the inverted 'Output1' signal at the D input is reproduced as the 'Input1' signal at the Q output terminal when: (i) 'Output2' is a logic low (i.e., the pressure within buffer chamber 18 is above 0.1 torr), or (ii) signal 'Sensor1' is a logic high (i.e., wafers are being processed in deposition chamber 24a), or (iii) signal 'Sensor2' is a logic high (i.e., wafers are being processed in deposition chamber 24b). The produced 'Input1' signal at the Q output terminal remains the last value of the inverted 'Output1' signal before: (i) 'Output2' becomes a logic high (i.e., the pressure within buffer chamber 18 is below approximately 0.1 torr), and (ii) signal 'Sensor1' becomes a logic low (i.e., wafers are not being processed in deposition chamber 24a), and (iii) 'Sensor2' becomes a logic low (i.e., wafers are not being processed in deposition chamber 24b).

Since the pressure within buffer chamber 18 during normal operation does not substantially exceed about $1.0 \times 10^{-7}$ torr, the 'Input1' signal is not asserted during normal operation when select switch 38 is in the automatic position. Only an increase in the pressure within buffer chamber 18 first passing through 0.05 torr then through 0.1 torr (e.g., venting of buffer chamber 18 during repair or preventive maintenance activities) will cause the 'Input1' signal to be asserted. When select switch 38 is placed in the manual position, pressing PM recovery switch 40 thereafter causes the D latch to produce and maintain an asserted 'Input1' signal at the Q output. The processing of wafers within deposition chamber 24a or 24b following a return to normal operation causes the 'Input2' signal to be asserted (i.e., enables data collection during wafer processing) and causes the 'Input1' signal to be deasserted (i.e., disables data collection during the recovery period).

It will be appreciated to those skilled in the art having the benefit of this disclosure that this invention is believed to be a measurement system for detecting the presence of one or more harmful chemical species within a chamber of a semiconductor wafer processing device. Furthermore, it is also to be understood that the form of the invention shown and described is to be taken as exemplary, presently preferred embodiments. Various modifications and changes may be made without departing from the spirit and scope of the invention as set forth in the claims. It is intended that the following claims be interpreted to embrace all such modifications and changes.

What is claimed is:

1. A measurement system for detecting the presence of a chemical species within a chamber of a semiconductor wafer processing device, comprising:

a sensor for sampling a gaseous environment within the chamber, wherein the sensor is coupled to receive a control signal and configured to produce a data signal in response to the control signal, and wherein the data signal is indicative of chemical species within the gaseous environment;

a control interface coupled to the sensor for producing the control signal and for receiving and thereafter providing the data signal (i) during the processing of a semiconductor wafer within the semiconductor wafer processing device, and (ii) following a maintenance activity performed upon the semiconductor wafer processing device;

a data collection computer coupled to receive the data signal from the control interface and configured to store the data signal; and wherein the control interface is coupled to receive a pressure signal, and wherein a present value of the pressure signal indicates normal operation of the semiconductor wafer processing device, and wherein past values of the pressure signal are indicative of the performance of a maintenance activity upon the semiconductor wafer processing device, and wherein the control interface is configured to assert the control signal dependent upon present and past values of the pressure signal.

2. The measurement system as recited in claim 1, wherein the semiconductor wafer processing device is a deposition system.

3. The measurement system as recited in claim 1, wherein the chemical species is selected from the group consisting of oxygen ($O_2$), nitrogen ($N_2$), and moisture ($H_2O$).

4. The measurement system as recited in claim 1, wherein the chemical species is an organic compound associated with photoresist processing.

5. The measurement system as recited in claim 1, wherein the chemical species is selected from the group consisting of oxygen ($O_2$), nitrogen ($N_2$), moisture ($H_2O$), isopropyl alcohol ($CH_3CH(OH)CH_3$), acetone ($CH_3COCH_3$), and ethyl-3-ethoxy propionate ($C_7H_{14}O_3$).

6. The measurement system as recited in claim 1, wherein the sensor is a quadrupole mass spectrometer detector.

7. The measurement system as recited in claim 1, wherein the control interface is coupled to receive a processing signal indicative of the processing of a semiconductor wafer within the semiconductor wafer processing device, and wherein the control interface is configured to assert the control signal dependent upon the processing signal.

8. A measurement system for detecting the presence of a chemical species within a deposition chamber of a deposition system, comprising:

a sensor for sampling a gaseous environment within the deposition chamber, wherein the sensor is coupled to receive a control signal, and wherein the sensor is configured to produce an analog data signal in response to the control signal, and wherein the analog data signal is indicative of the presence of the chemical species within the deposition chamber;

a control interface coupled to the sensor, wherein the control interface is configured to receive:

the analog data signal;

a processing signal indicative of the processing of a semiconductor wafer within the deposition chamber; and a first pressure signal, wherein a present value of the first pressure signal is indicative of normal operation of the deposition system, and wherein past values of the first pressure signal are indicative of the performance of a maintenance activity upon the deposition chamber;

wherein the control interface is configured to convert the analog data signal to a digital data signal and to provide the digital data signal, and wherein the control interface is configured to produce the control signal dependent upon the processing signal and the present and past values of the first pressure signal; and a data collection computer coupled to receive the digital data signal from the control interface and to store the digital data signal.

9. The measurement system as recited in claim 8, wherein the sensor is a quadrupole mass spectrometer detector.

10. The measurement system as recited in claim 8, wherein the chemical species is selected from the group consisting of oxygen ($O_2$), nitrogen ($N_2$), and moisture ($H_2O$).

11. The measurement system as recited in claim 8, wherein the chemical species is an organic compound associated with photoresist processing.

12. The measurement system as recited in claim 8, wherein the chemical species is selected from the group consisting of oxygen ($O_2$), nitrogen ($N_2$), moisture ($H_2O$), isopropyl alcohol ($CH_3CH(OH)CH_3$), acetone ($CH_3COCH_3$), and ethyl-3-ethoxy propionate ($C_7H_{14}O_3$).

13. The measurement system as recited in claim 8, wherein the processing signal is produced by a processing sensor.

14. The measurement system as recited in claim 8, wherein the first pressure signal is produced by a manometer.

15. The measurement system as recited in claim 8, wherein the control interface comprises:

a logic controller coupled between the sensor and the data collection computer, wherein the logic controller is coupled to receive the first pressure signal, a maintenance signal indicative of the performance of maintenance upon the deposition system, and the processing signal, and wherein the logic controller is configured to produce the control signal and a second and third pressure signals dependent upon the first pressure signal; and a logic circuit coupled to the logic controller and coupled to receive the processing signal and the second and third pressure signals, wherein the logic circuit is configured to produce the maintenance signal dependent upon the second and third pressure signals.

16. The measurement system as recited in claim 15, wherein the logic controller asserts the second pressure signal when the first pressure signal indicates a pressure greater than a first threshold value, and wherein the logic controller asserts the third pressure signal when the first pressure signal indicates a pressure greater than a second threshold value, and wherein the second threshold value is greater than the first threshold value, and wherein both the first and second threshold values exceed a normal operating pressure.

17. The measurement system as recited in claim 16, wherein the first threshold value is about 0.05 torr, the second threshold value is approximately 0.1 torr, and the normal operating pressure is about $1.0 \times 10^{-7}$ torr.

18. The measurement system as recited in claim 16, wherein the logic circuit asserts the maintenance signal when both the first and second pressure signals are asserted and the first pressure signal is asserted before the second pressure signal, indicating an increase in first pressure signal above the normal operating pressure due to maintenance performed upon the deposition system.

19. The measurement system as recited in claim 18, wherein once the logic circuit asserts the maintenance signal, the logic circuit continues to assert the maintenance signal until the first pressure signal indicates a return to normal operation and the processing signal indicates the processing of a semiconductor wafer within the deposition chamber.

20. The measurement system as recited in claim 15, wherein the logic circuit comprises a select switch and a maintenance switch, and wherein the select switch comprises an automatic position and a manual position, and wherein when the select switch is in the automatic position the logic circuit is configured to produce the maintenance signal dependent upon the second and third pressure signals, and wherein when the select switch is in the manual position the logic circuit is configured to produce the maintenance signal when a user activates the maintenance switch.

21. The measurement system as recited in claim 15, wherein the sensor is a quadrupole mass spectrometer detector operating in either a scanning mode, an idle mode, or a shutdown mode dependent upon the control signal.

22. The measurement system as recited in claim 21, wherein the sensor produces the analog data signal when operating in the scanning mode, and wherein the logic controller issues the control signal placing the sensor in the scanning mode when the value of the first pressure signal is less than a threshold value and the processing signal is asserted.

23. The measurement system as recited in claim 22, wherein the threshold value is about 0.01 torr.

24. The measurement system as recited in claim 23, wherein the logic controller issues the control signal placing the sensor in the scanning mode when the value of the first pressure signal exceeds the threshold value and the maintenance signal is asserted.

25. The measurement system as recited in claim 23, wherein the logic controller issues the control signal placing the sensor in the idle mode when the value of the first pressure signal is less than the threshold value and both the processing and maintenance signals are deasserted.

26. The measurement system as recited in claim 23, wherein the logic controller issues the control signal placing the sensor in the shutdown mode when the value of the first pressure signal is greater than the threshold value.

* * * * *